United States Patent [19]

Summers et al.

[11] Patent Number: 4,964,864
[45] Date of Patent: Oct. 23, 1990

[54] HEART ASSIST PUMP

[75] Inventors: David P. Summers; Jeddy D. Nixon, both of Houston, Tex.

[73] Assignee: American Biomed, Inc., The Woodlands, Tex.

[21] Appl. No.: 249,830

[22] Filed: Sep. 27, 1988

[51] Int. Cl.⁵ ............................................. A61M 1/10
[52] U.S. Cl. ..................................... 623/3; 600/16
[58] Field of Search ................... 623/3; 600/16, 17, 18

[56] References Cited

U.S. PATENT DOCUMENTS

| | | | |
|---|---|---|---|
| 3,505,987 | 4/1970 | Heilman | 623/3 |
| 3,667,069 | 6/1972 | Blackshear et al. | 623/3 |
| 4,051,840 | 10/1977 | Kantrowitz et al. | 623/3 |
| 4,102,610 | 7/1978 | Taboada et al. | 623/3 |
| 4,173,796 | 11/1979 | Jarvik | 623/3 |
| 4,382,199 | 5/1983 | Isaacson | 623/3 |
| 4,625,712 | 12/1986 | Wampler | 623/3 |
| 4,817,586 | 4/1989 | Wampler | 600/16 |

FOREIGN PATENT DOCUMENTS 2184785A 7/1987 United Kingdom .

OTHER PUBLICATIONS

Medical Societies, Feb. 14, 1959.

*Primary Examiner*—Randall L. Green
*Assistant Examiner*—Stephanie L. Iantorno
*Attorney, Agent, or Firm*—Gunn, Lee & Miller

[57] ABSTRACT

A temporary circulatory assist pump is disclosed for implantation in the heart of a patient through the femoral artery. The pump is driven by a flexible drive shaft extending through a catheter and being connected to a power source outside the body of the patient. The pump utilizes the moineau pumping principal to pump blood at a rate of approximately three to four liters per minute through the circulatory system of the patient.

5 Claims, 3 Drawing Sheets

HEART ASSIST PUMP

BACKGROUND OF THE DISCLOSURE

This invention relates to blood pumps, particularly to a temporary circulatory assist pump adapted for insertion into the vascular system of a patient to provide temporary circulatory assistance for an infarcted left or right ventricle of the heart.

Death and disability from heart disease are most commonly due to the pumping inadequacy of an infarcted left or right ventricle. The heart of a patient suffering from this condition functions in all other respects but does not provide sufficient blood flow to keep the patient alive. Typically, a patient suffering from this condition would require major surgery to maintain the heart and provide sufficient blood flow for the patient.

Another area where temporary circulatory assistance may be required is in allograft cardiac replacement or heart transplants. Although one year survivals after a heart transplant now approach 80%, a great many patients die waiting for a transplant, as do many of the 20% who might be saved by circulatory assistance while immunosuppressive agents are combating the body's natural rejection response of a transplanted heart. There is a great need for an effective circulatory assist pump for maintaining the life of a patient until the transplant can be accomplished and the allograft is stabilized. As the average life expectancy of the U.S. population continues to increase, coronary artery disease and chronic congestive heart failure can be expected to significantly increase the utilization of mechanical circulatory assistance. A realistic estimate of the number of potential candidates for mechanical circulatory assistance would be approximately 300,000 patients each year in the United States.

Methods and apparatus exist in the prior art for circulatory assistance of a heart. In U.S. Pat. No. 4,625,712 a high capacity intravascular blood pump is disclosed. The pump is inserted into the heart through the femoral artery and driven via a flexible cable from an external power source. The drive cable is contained within a catheter attached to the pump. The pump is rotated in the range of 10,000-20,000 rpm to produce blood flow on the order of about 4 liters per minute.

U.S. Pat. No. 3,505,987 discloses a counterpulsation system for aiding coronary circulation. The system includes an expandable impeller located within the aorta of a patient. The impeller is expanded and contracted while simultaneously being reciprocated within the aorta and synchronized with the pumping activity of the heart for reducing aortic pressure during systole and increasing aortic pressure during diastole.

U.S. Pat. No. 3,667,069 discloses an implantable jet pump for replacing or assisting the right heart. The jet pump comprises an elongated tubular structure including an upstream driving nozzle from which a driving flow of arterial blood under pressure is ejected into a suction nozzle creating its own reduced pressure to cause venous blood to be sucked into and admixed with the driving flow for distribution to the pulmonary circulation system. The jet pump may be powered by blood pumped from the left heart or an artificial replacement for the left heart.

U.S. Pat. No. 4,051,840 discloses an aortic patch which may be surgically implanted in the thoracic aorta. The aortic patch is systematically inflated and deflated to generate pressure waves in the blood stream. The pressure waves assist the heart by augmenting the circulation of the blood to the body.

Generally, the methods available for circulatory assistance of the heart require major surgery for the implantation of the device which presents a great risk to the survival of the patient. The device disclosed in U.S. Pat. No. 4,625,712 may be introduced into the heart through the femoral artery thus avoiding major surgery and reducing the risk to the patient. However, adequate blood flow requires that the pump and drive shaft be rotated at extremely high rpm through the bends and sharp curves of the femoral artery. Extreme care must be taken to avoid creation of hot spots in the femoral arteries. The prior art has thus been unable to provide an easily implanted low risk temporary circulatory assist pump capable of providing sufficient blood flow to assist a heart so that the heart may heal itself or keep the patient alive while waiting for a transplant to become available.

SUMMARY OF THE INVENTION

The present invention is directed to a miniature temporary circulatory assist pump adapted to be inserted in the heart of the patient for circulatory assistance. The pump is introduced into the left ventricle of the heart by a catheter passed through the arterial system of the patient. The pump utilizes the moineau pump principle to deliver large volumes of blood at relatively low rpm and pressure. In an embodiment of the invention, a venturi tube arrangement is utilized to pressurize the blood flow to create a suction effect for increasing the volume of blood pumped through the circulatory system of the patient.

DETAILED DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
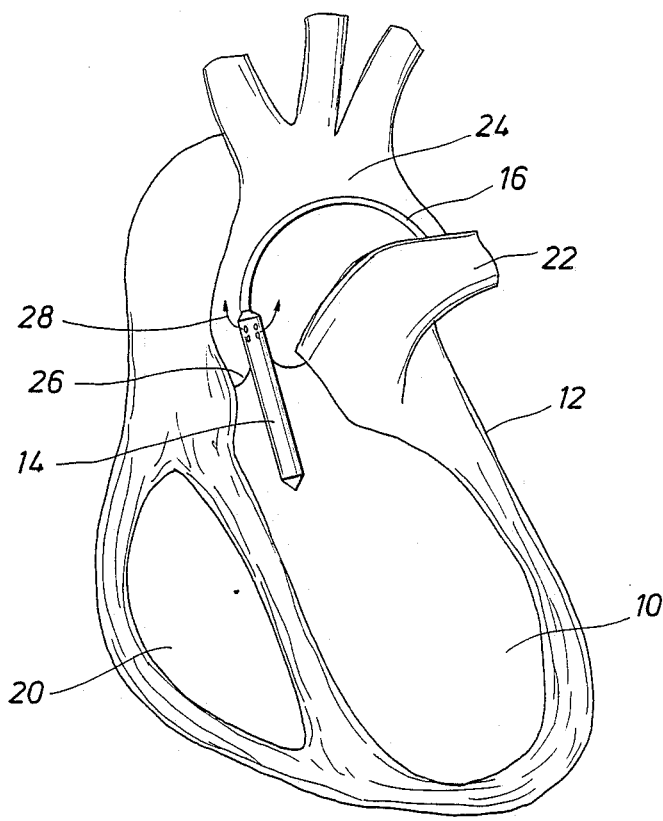
FIG. 1 is an illustrative view of a section of a human heart depicting the preferred position of the pump of the invention in the left ventricle of the heart.
Figure 2:
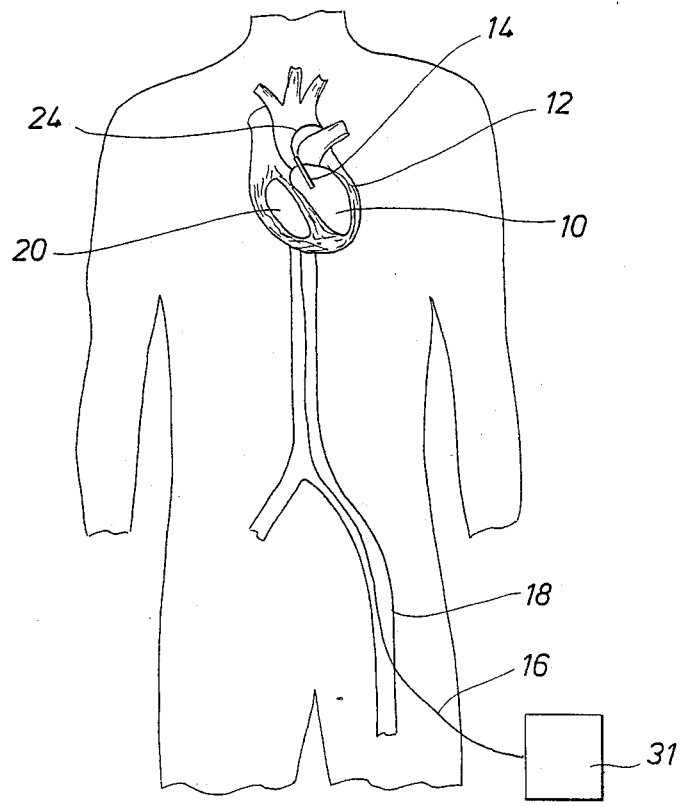
FIG. 2 is a schematic view illustrating the insertion of the pump of the invention through the femoral artery of a patient.

Referring first to FIGS. 1 and 2 of the drawings, the blood pump of the invention is shown inserted in the left ventricle 10 of the heart 12. The blood pump is generally identified by the reference numeral 14 and is carried at the forward end of a catheter 16. Access to the heart 12 is provided in the preferred embodiment through the femoral artery 18. This is the preferred insertion point, however, it is understood that the heart 12 may be accessed through other arteries or other surgical means. In the preferred embodiment, the blood pump 14 is located in the left ventricle 10. However, in some circumstances it may be desirable to locate the blood pump 14 in the right ventricle 20. Access to the right ventricle 20 may be provided through the pulmonary artery 22. In operation, the intake end of the blood pump 14 shown in FIG. 1 is located within the left ventricle 10. The outlet or discharge end of the blood pump 14 is located in the aorta 24. The blood pump 14 thus extends partially into the left ventricle 10 through the heart valve 26. Blood is pumped through the blood pump 14 from the left ventricle 10 in the direction of the arrows 28 into the aorta 24.

Figure 6:
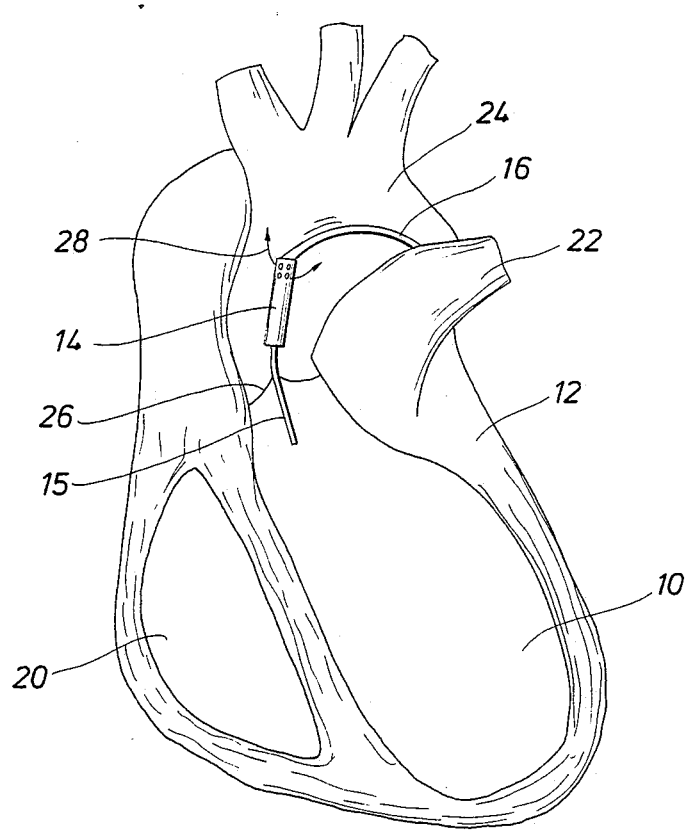
FIG. 6 is an illustrative view of a section of a human heart depicting an alternate embodiment of the pump of the invention.

In some patients, it may not be desirable to position the pump 14 within the left ventricle 10. In those circumstances, the pump 14 is provided with a suction tube 15 mounted to the intake end of the pump 14. The suction tube 15 is formed of a flexible, elastomeric material and projects from the intake end of the pump 14 into the left ventricle 10 of the heart 12 as shown in FIG. 6.

Figure 3:
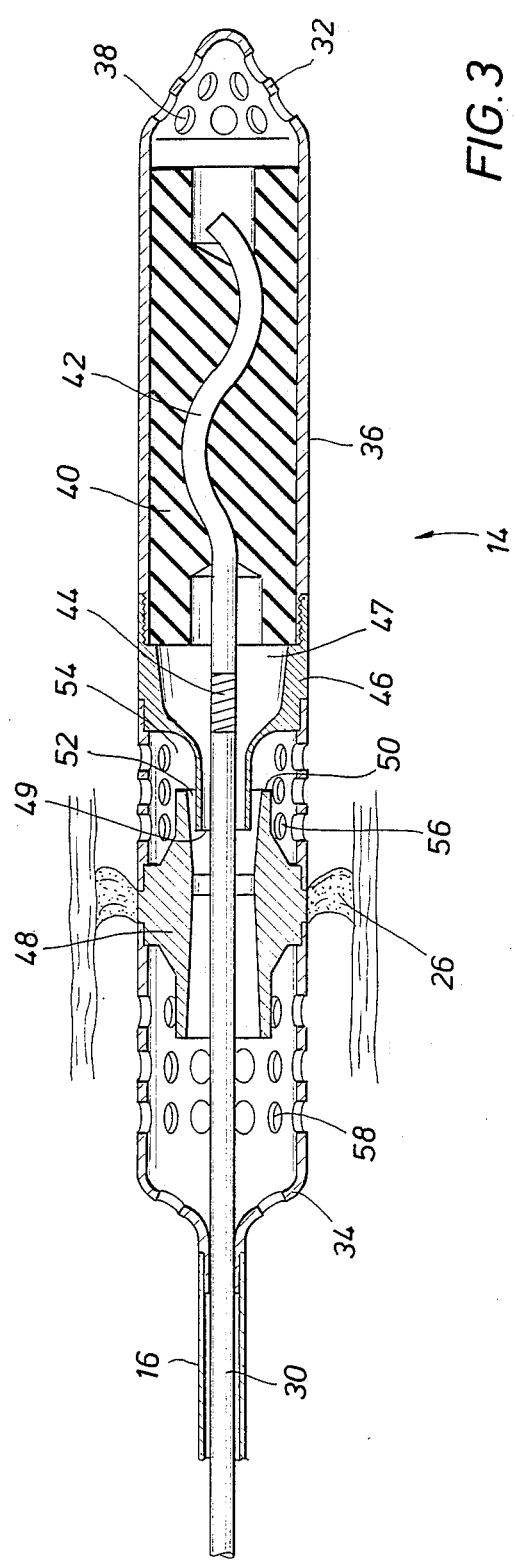
FIG. 3 is a partial sectional view of the pump of the invention.

Referring now to FIG. 3, the pump 14 is shown in greater detail. The pump 14 is driven by a flexible drive shaft 30 which extends through the catheter 16. The drive shaft 30 is driven by a motor 31 located outside the patient's body, as best shown in FIG. 2. The pump 14 is secured to the distal end of the catheter 16. The pump 14 and catheter 16 are guided through the femoral artery to the left ventricle 10. When the left ventricle 10 is reached, the pump 14 is positioned in the left ventricle 10 of the heart. Utilizing known insertion techniques, the pump 14 is positioned so that the intake end 32 extends through the heart valve 26 into the left ventricle 10. The discharge end 34 of the pump 14 is positioned outside the left ventricle 10 so that pumped blood is discharged into the aorta 24 as shown in FIG. 1.

In the embodiment of the invention shown in FIG. 3, the pump 14 comprises a substantially cylindrical elongate body 36. The intake end 32 of the body 36 presents a cone-like profile blunted at its forward end so that it may easily be inserted into the left ventricle 10 past the heart valve 26 without damaging the heart valve or any of the heart tissue. The intake end 32 includes a number of intake ports 38 so that blood collected in the left ventricle 10 may flow freely into the pump 14. Housed within the housing 36 is a stator 40 and a rotor 42. The stator and rotor operate utilizing the moineau pumping principle which uses rotary motion to move a seal continuously through the stator 40 for pumping blood through the pump 14. The stator 40 is fabricated of resilient material and the rotor 42 is fabricated of stainless steel material formed in a helical shape. The rotor 42 is connected to the drive shaft 30 by a flexible joint 44 which permits the end of the rotor 42 to move through a helical path as the rotor 42 is driven by the drive shaft 30.

At the discharge end of the stator 40, a discharge nozzle 46 is provided for directing the pumped blood to the intake end 50 of a venturi tube 48. It will be observed that the discharge end of the discharge nozzle 46 extends into the intake end 50 of the venturi tube 48. An annular space 52 is thus defined between the discharge end 49 of the discharge nozzle 46 and the intake end 50 of the venturi tube 48. The intake end 50 of the venturi tube 48 is open to a chamber 54 formed within the housing 36 about the discharge nozzle 46 and venturi tube 48. Blood collected in the left ventricle 10 enters the chamber 54 through a plurality of ports 56.

In operation, blood from the left ventricle 10, in the embodiment of FIG. 3, is sucked through the intake 32 and pumped into the discharge nozzle 46 by rotation of the rotor 42. The blood is pressurized as it is pumped through the discharge nozzle 46 by restricting the discharge area of the discharge nozzle 46 and thereby jetting the blood into the venturi tube 48. The restriction in the discharge nozzle 46 and venturi tube 48 are designed to cause the pumped blood passing through the discharge nozzle 48 to attain venturi velocities which can be precisely determined. At venturi velocities, negative pressure is produced in the annular space 52 around the discharge end 49 of the discharge nozzle 46. Thus, blood collected in the chamber 56, which is open to the left ventricle 10, is sucked into the venturi tube 48 through the intake end 50 and admixed with the blood flow discharged through the discharge nozzle 46. The outlet end of the venturi tube 48 tapers outwardly, as shown in FIG. 3. The downstream pressure in the venturi tube 48 is thus reduced as the cross-sectional area of the venturi tube 48 increases. The blood pressure at the outlet end of the venturi tube 48 is reduced so that it is equal to intake pressure at the intake end 32 of the pump 14. In this manner, a larger volume of blood may be pumped through the pump 14 at low pressure. For example, the pump 14 at its intake end 32 may be moving one liter of blood per minute at three psi. However, as this blood volume is passed through the discharge nozzle 46 into the venturi tube 48 the pressure in the venturi tube 48 increases to nine psi, thereby creating negative pressure in the annular space 52. The negative pressure draws an additional two liters of blood from the chamber 54 into the s&:ream of blood pumped into the venturi tube 48. The pressure drops back to three psi at the discharge end of the venturi tube 48. By passing the pumped blood through the venturi tube 48, three liters of blood per minute is pumped by the pump 14 at three psi. The blood is discharged into the aorta 24 through outlet ports 58 formed in the discharge end 34 of the pump 14.

Figure 4:
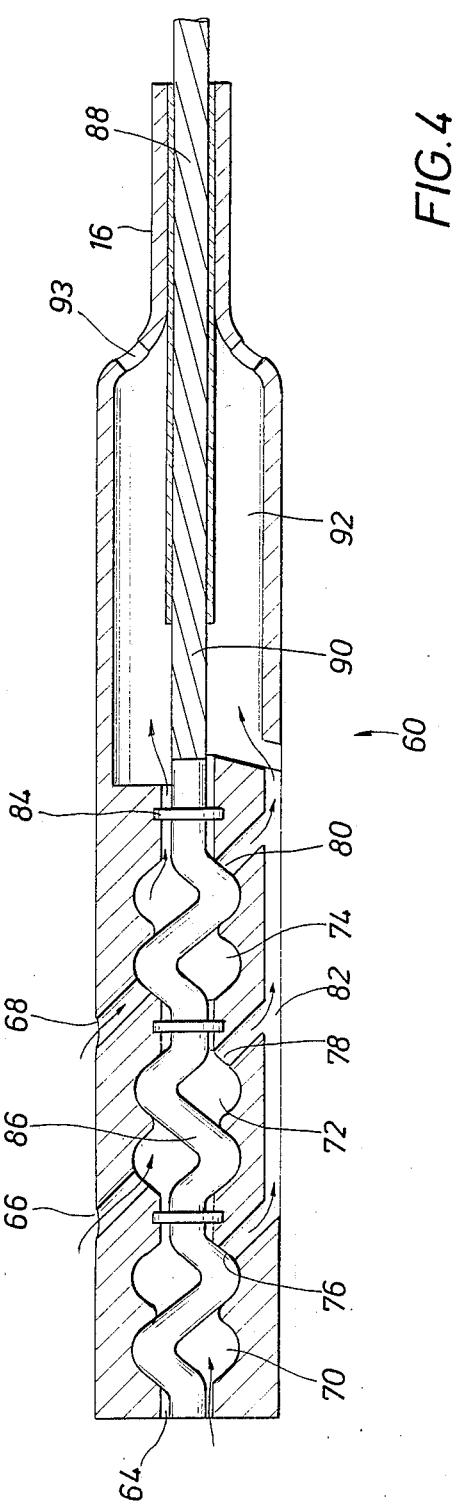
FIG. 4 is a partial sectional view of an alternate embodiment of the pump of the invention.

Referring now to FIG. 4, an alternate embodiment of the pump of the invention generally identified by the reference numeral 60 is shown. The pump 60 utilizes the same moineau type pumping principal to move blood through the pump, however, the stator and rotor are modified somewhat as will be described in greater detail. The pump 60 is positioned in the left ventricle 10 of the heart 12 by the catheter 16 in the same manner as previously described with regard to pump 14.

The pump 60 is very similar to the pump 14 and therefore like reference numerals are used to indicate like elements. The stator 62 of the pump 60, however, is provided with multiple suction intake ports which discharge into a common discharge duct. The stator 62 is fabricated of a resilient material and includes three intake ports 64, 66 and 68. The intake port 64 is located at the forward end of the stator 64. The intake ports 66 and 68 are located on the cylindrical body of the stator 62 and are formed by drilling a hole at an angle through the body 62 opening into a rotor cavity. Each of the intake ports 64, 66 and 68 communicate with separate rotor cavities 70, 72 and 74, respectively, which form the rotor cavity of the pump 60. The rotor cavities 70, 72 and 74 include outlet ports 76, 78 and 80 which discharge into a common discharge duct 82. The rotor cavities 70, 72 and 74 are separated by shaft stabilizers 84 which support and seal about the rotor 86 within the rotor cavity of the pump 60. The rotor 86 is driven by drive shaft 88 which is connected to the drive motor 31. The drive shaft 88 is connected to the rotor 86 by a flexible joint 90 which permits the end of the rotor 86 to move through a slight orbital path as the rotor 86 is rotated by the drive shaft 88.

The pump 60 shown in FIG. 4, comprises a single rotor and stator having multiple inlet and outlet ports so that a greater volume of blood is pumped through the pump 60 with each revolution of the rotor 86. The rotor cavities 70, 72 and 74 are configured for separate and individual pumping upon rotation of the rotor 86. In operation, rotation of the rotor 86 by the drive shaft 88 moves a seal continuously through each of the cavities 70, 72 and 74. As the rotor 86 rotates, blood enters the rotor cavities 70, 72 and 74 through the intake ports 64, 66 and 68. Each rotation of the rotor 86 sweeps the rotor cavities 70, 72 and 74 and forces the blood through the outlet ports 76, 78 and 80 into the common discharge duct 82 and then into the conduit 92 which discharges into the aorta 24 through outlet ports 93.

Figure 5:
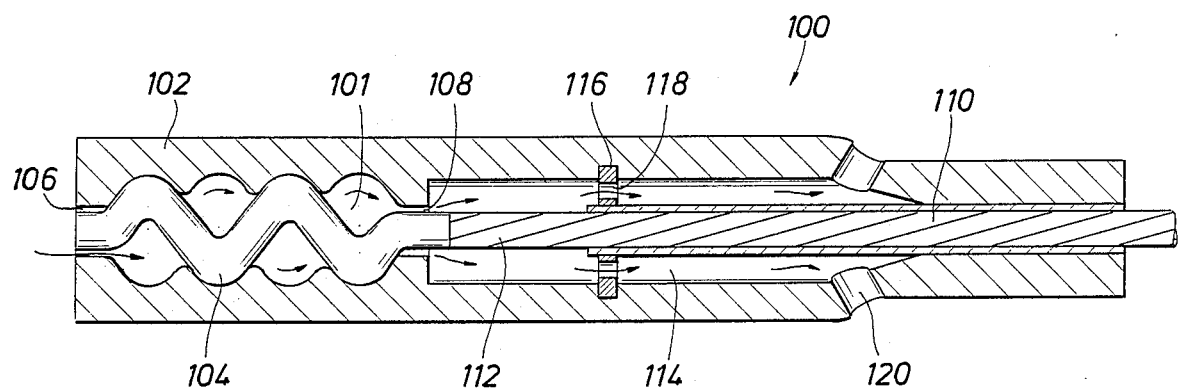
FIG. 5 is a partial sectional view of an alternate embodiment of the pump of the invention.

Referring now to FIG. 5, an alternate embodiment of the heart assist pump of the invention is shown. The pump 100 is substantially identical to the pump 60 shown in FIG. 4. It is placed in the left ventricle 10 of the heart 12 substantially the same manner as previously described. The pump 100 comprises a stator 102 which houses a rotor 104. The stator 102 is fabricated of resilient material so that a rotating seal is formed with the helical shaped stainless steel rotor 104. The stator 102 includes a helical rotor cavity 101 having an intake port 106 and an outlet port 108. The rotor 104 is connected to a drive shaft 110 by a flexible joint 112. The drive shaft 110 is centrally positioned within the discharge conduit 114 of the pump 100 by a shaft stabilizer 116.

In operation, the pump 100 draws blood from the left ventricle 10 through the intake port 106. As the rotor 104 rotates, a moving seal is formed with the stator 102 so that blood is pumped through the helical cavity 102 and discharged into the conduit 114. The shaft stabilizer 116 includes a plurality of apertures 118 extending therethrough permitting blood to flow past the shaft stabilizer 116 to be discharged into the aorta 24 through outlet ports 120 located in the rear wall of the the pump 100.

The heart assist pump of the present invention utilizes the geometrical relationship between the rotor and the stator to pump blood from the heart of a patient. In cross-section, the rotor and stator are in contact with each other at two points which form two sealing lines over the length of the rotor and stator. The rotor has a single helix shape and is typically fabricated of a metallic material. The stator is formed as a double helix and is typically fabricated of an elastomer. The interference or compression fit between the rotor and stator creates a series of sealed chambers or cavities. Pumping action is achieved by the rotor driven eccentrically within the stator. Fluid, such as blood, enters the cavity formed at the inlet end of the pump and progresses within the cavity and is discharged through the outlet end. Because the force generating sections of the rotor and stator are smooth and curved, very little surface area is available for contact stress. In cross-section, the stator is obround while the rotor in cross-section is circular. The dissimilarity of the shapes between the rotor and stator creates wedge-shaped cavities within the pump unit. Rotation exerts a progressive displacement of the wedge-shaped cavities. In doing so, blood seeks an exit without turbulence. Thus, the volume of blood flowing through the pump of the invention is directly proportional to rotor speed. Blood contained in the sealed cavities which are formed as the rotor turns is displaced axially and with complete continuity from the suction or inlet end to the outlet end of the pump. Despite the fact that the rotor rotates, no turbulence is produced. The constant volume of the enclosed cavities eliminates pressurizing forces and thus a low surge pumping action is accomplished which is ideal for shear sensitive materials.

The pump of the present disclosure is self-priming and non-cavitating. The prime creates the suction movement of material without which the material cannot be moved. A progressive cavity pump of the type disclosed herein is always in prime. Impeller pumps, however, loose prime and over-accelerate. Over-acceleration can produce cavitation within the pump, resulting in pockets of partial vacuums in the blood flow, causing the separation of blood parts. Blood, being a non-Newtonian fluid, is more susceptible to such spontaneous, non-linear viscoelastic behavior. In viscometric fluid motion, each fluid element is undergoing a steady sheering motion. However, in non-linear viscoelastic responses, the symmetry of a simple flow is replaced by functional stress factors and turbulence with loss of efficiencies. More simply stated, the heart assist pump of the present disclosure maintains a nonturbulent, constant volume of blood in the enclosed cavities with no pressurizing forces. The low surge action of the pump disclosed herein produces an ideal flow with very predictable Newtonian flow regiments.

The pump of the present invention is dimensioned to provide blood flow of three to four liters per minute, yet it operates at a speed of approximately 2,500 rpm to produce the required blood flow to sustain a patient while the patient's heart is resting and repairing itself. The pump of the present disclosure does not utilize propellers or turbine blades to pump blood. The moineau type pump of the present invention substantially reduces or eliminates the risk of hemolysis. The blood is pumped through the pump of the invention by a rotating seal formed between the stator and helical rotor as described above. The blood is thus pushed through the stator cavity with each rotation of the rotor. No shear forces are developed that would damage the blood cells as the blood is pumped through the pump and discharged into the aorta of the patient.

While the foregoing is directed to the preferred embodiment of the present invention, other and further embodiments of the invention may be devised without departing from the basic scope thereof, and the scope thereof is determined by the claims which follow.

What is claimed is:

1. A temporary circulatory assist pump, comprising:
   (a) an elongate, cylindrical biocompatible pump having at least one intake port and at least one discharge port, said pump being sized for passage through a human blood vessel and insertion in to a heart;
   (b) said pump comprising a stator and a rotor whereby orbiting motion of the rotor moves a seal continuously through the stator for pumping of blood therethrough;

(c) wherein said stator and rotor define an axial cavity divided to form separate rotor cavities having separate outlet ports for discharging blood into a discharge duct in fluid communication with said separate rotor cavities;

(d) extravascular power means connected to said pump for driving said rotor; and (e) drive shaft means connecting said pump means to said power means, said drive shaft means being connected to said rotor by a flexible joint, said flexible joint permitting flexure deformation thereby enabling said rotor to move through an orbital path upon rotation of said rotor by said power means.

2. The pump of claim 1 including a discharge nozzle supported within said housing in line with said stator, said discharge nozzle including a restriction for pressurizing and jetting blood pumped therethrough.

3. The pump of claim 1 wherein said pump means comprises a stator fabricated of resilient material and a helical shaped stainless steel rotor rotatable within said stator, said stator and said rotor cooperating to form a moving seal continuously through said stator upon rotation of said rotor.

4. The pump of claim 1 wherein said pump includes at least two separate intake ports in fluid communication with said separate rotor cavities formed in said pump.

5. The pump of claim 4 wherein said separate rotor cavities are separated by at least one shaft stabilizer supporting said rotor within said stator.

* * * * *